United States Patent
Havelund et al.

(10) Patent No.: US 9,387,176 B2
(45) Date of Patent: Jul. 12, 2016

(54) METHOD FOR DRYING A PROTEIN COMPOSITION, A DRIED PROTEIN COMPOSITION AND A PHARMACEUTICAL COMPOSITION COMPRISING THE DRIED PROTEIN

(75) Inventors: Svend Havelund, Bagsværd (DK); Simon Bjerregaard Jensen, Hillerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 780 days.

(21) Appl. No.: 12/598,279

(22) PCT Filed: Apr. 30, 2008

(86) PCT No.: PCT/EP2008/055306
§ 371 (c)(1),
(2), (4) Date: Mar. 25, 2010

(87) PCT Pub. No.: WO2008/132224
PCT Pub. Date: Nov. 6, 2008

(65) Prior Publication Data
US 2010/0179090 A1    Jul. 15, 2010

Related U.S. Application Data

(60) Provisional application No. 60/927,086, filed on May 1, 2007, provisional application No. 60/977,424, filed on Oct. 4, 2007.

(30) Foreign Application Priority Data

Apr. 30, 2007 (EP) .................................... 07107221
Oct. 3, 2007 (EP) .................................... 07117798

(51) Int. Cl.
*A61K 38/28*    (2006.01)
*A61K 9/16*    (2006.01)
*A61K 38/26*    (2006.01)

(52) U.S. Cl.
CPC ............... *A61K 9/1688* (2013.01); *A61K 38/26* (2013.01); *A61K 38/28* (2013.01)

(58) Field of Classification Search
CPC ....... A61K 38/26; A61K 38/28; C07K 14/605
See application file for complete search history.

(56) References Cited

U.S. PATENT DOCUMENTS

| | | | |
|---|---|---|---|
| 2,832,685 A * | 4/1958 | Scott | 426/580 |
| 3,528,960 A | 9/1970 | Haas et al. | |
| 3,719,655 A | 3/1973 | Jackson | |
| 3,869,437 A | 3/1975 | Lindsay et al. | |
| 3,950,517 A | 4/1976 | Lindsay et al. | |
| 4,033,941 A | 7/1977 | Stilz et al. | |
| 4,179,337 A | 12/1979 | Davis et al. | |
| 5,053,389 A * | 10/1991 | Balschmidt et al. | 514/6.1 |
| 5,179,189 A | 1/1993 | Domb et al. | |
| 5,359,030 A | 10/1994 | Ekwuribe | |
| 5,478,575 A | 12/1995 | Miyazaki et al. | |
| 5,506,202 A | 4/1996 | Vertesy et al. | |
| 5,506,203 A | 4/1996 | Bäckström et al. | |
| 5,898,067 A | 4/1999 | Balschmidt et al. | |
| 5,922,675 A | 7/1999 | Baker et al. | |
| 6,221,837 B1 | 4/2001 | Ertl et al. | |
| 6,251,856 B1 | 6/2001 | Markussen et al. | |
| 6,451,349 B1 * | 9/2002 | Robinson et al. | 424/489 |
| 6,500,645 B1 | 12/2002 | Kjeldsen et al. | |
| 6,770,625 B2 | 8/2004 | Soltero et al. | |
| 6,867,183 B2 | 3/2005 | Soltero et al. | |
| 6,869,930 B1 | 3/2005 | Havelund et al. | |
| 6,902,744 B1 * | 6/2005 | Kolterman et al. | 424/489 |
| 7,030,082 B2 | 4/2006 | Soltero et al. | |
| 7,030,083 B2 | 4/2006 | Schreiner et al. | |
| 2001/0041786 A1 * | 11/2001 | Brader et al. | 530/300 |
| 2002/0045731 A1 | 4/2002 | Schaffer et al. | |
| 2003/0027748 A1 | 2/2003 | Ekwuribe et al. | |
| 2003/0035775 A1 | 2/2003 | Klibanov | |
| 2003/0083232 A1 | 5/2003 | Soltero et al. | |
| 2003/0104981 A1 | 6/2003 | Mandic | |
| 2003/0134294 A1 | 7/2003 | Sandford et al. | |
| 2003/0166508 A1 | 9/2003 | Zhang | |
| 2004/0038867 A1 | 2/2004 | Still et al. | |
| 2004/0097410 A1 | 5/2004 | Zheng et al. | |
| 2004/0198949 A1 | 10/2004 | Ekwuribe et al. | |
| 2004/0254119 A1 | 12/2004 | West et al. | |
| 2005/0276843 A1 | 12/2005 | Quay et al. | |
| 2006/0019874 A1 | 1/2006 | Radhakrishnan et al. | |
| 2006/0183668 A1 | 8/2006 | Jonassen et al. | |

(Continued)

FOREIGN PATENT DOCUMENTS

| CN | 1187119 A | 7/1998 |
|---|---|---|
| CN | 1314818 A | 9/2001 |

(Continued)

OTHER PUBLICATIONS

Glucagon for Injection, Marked-up Physician Package Insert, Eli Lilly and Company, Sep. 8, 1998.*
EXUBERA (insulin human [rDNA origin]) Inhalation Powder, US Package Insert, Jan. 27, 2006.*
Lai et al. "Solid-State Chemical Stability of Proteins and Peptides" Journal of Pharmaceutical Sciences, vol. 88, No. 5, May 1999, pp. 489-500.*
Farag Badway et al. "Microenvironmental pH Modulation in Solid Dosage Forms," Journal of Pharmaceutical Sciences, vol. 96, No. 5, May 2007, pp. 948-959, published online Apr. 23, 2007.*
Kane et al., Physics ed.3, pp. 365 and 6-77.
Lewis, Hawley's Condensed Chemical Dictionary, 1993, vol. 12, p. 1101.

(Continued)

*Primary Examiner* — Christina Bradley
(74) *Attorney, Agent, or Firm* — Jianjie Hu

(57) ABSTRACT

The present invention relates to a method for spray-drying of protein solutions and the spray-dried protein product. The invention also relates to pharmaceutical compositions containing such spray-dried protein, to methods of treating diabetes and hyperglycaemia using the spray-dried protein of the invention and to the use of such spray-dried protein in the treatment of diabetes and hyperglycaemia.

8 Claims, No Drawings

(56) References Cited

U.S. PATENT DOCUMENTS

| | | |
|---|---|---|
| 2008/0076705 A1 | 3/2008 | Kodra et al. |
| 2010/0009898 A1 | 1/2010 | Nielsen et al. |
| 2011/0105720 A1 | 5/2011 | Madsen et al. |
| 2014/0073564 A1 | 3/2014 | Madsen et al. |

FOREIGN PATENT DOCUMENTS

| | | |
|---|---|---|
| CN | 1317958 A | 10/2001 |
| CN | 1390854 | 1/2003 |
| EP | 214826 | 3/1987 |
| EP | 265213 | 4/1988 |
| EP | 376156 | 7/1990 |
| EP | 511600 | 11/1992 |
| EP | 544466 | 6/1993 |
| EP | 712861 | 5/1996 |
| EP | 712862 | 5/1996 |
| EP | 925792 | 6/1999 |
| EP | 1002547 | 5/2000 |
| EP | 1121144 | 6/2002 |
| EP | 894095 | 5/2003 |
| GB | 894095 | 4/1962 |
| GB | 1492997 | 11/1977 |
| JP | 57-067548 | 4/1982 |
| JP | H01500116 | 1/1989 |
| JP | 1-254699 | 10/1989 |
| JP | 9-502867 | 3/1997 |
| JP | 10-509176 | 9/1998 |
| JP | 11-502110 | 2/1999 |
| JP | 2000-501419 | 2/2000 |
| JP | 2000-504732 | 4/2000 |
| JP | 2001-521004 | 11/2001 |
| JP | 2001-521006 | 11/2001 |
| JP | 2001-521904 | 11/2001 |
| JP | 2002-308899 | 10/2002 |
| JP | 2002-543092 | 12/2002 |
| WO | WO 90/01038 | 2/1990 |
| WO | WO 91/12817 | 9/1991 |
| WO | WO 92/00321 | 1/1992 |
| WO | WO 92/01476 | 2/1992 |
| WO | WO 92/12999 | 8/1992 |
| WO | WO 94/08599 | 4/1994 |
| WO | WO 95/07931 | 3/1995 |
| WO | WO 95/13795 | 5/1995 |
| WO | WO 95/24183 | 9/1995 |
| WO | WO 96/15803 | 5/1996 |
| WO | WO 96/29344 | 9/1996 |
| WO | WO 96/37215 | 11/1996 |
| WO | WO 97/31022 | 8/1997 |
| WO | WO 98/01473 | 1/1998 |
| WO | WO 98/02460 | 1/1998 |
| WO | WO 99/21888 | 5/1999 |
| WO | WO 99/24071 | 5/1999 |
| WO | WO 99/65941 | 12/1999 |
| WO | WO 00/00176 | 1/2000 |
| WO | WO 00/10541 | 3/2000 |
| WO | WO 00/23098 | 4/2000 |
| WO | WO 00/42993 | 7/2000 |
| WO | WO 00/43034 | 7/2000 |
| WO | WO 00/61178 | 10/2000 |
| WO | WO 00/78302 | 12/2000 |
| WO | WO 02/094200 | 11/2002 |
| WO | WO 02/098232 | 12/2002 |
| WO | WO 02/098446 | 12/2002 |
| WO | WO 03/013573 | 2/2003 |
| WO | WO 03/022208 | 3/2003 |
| WO | WO 03/022996 | 3/2003 |
| WO | WO 03/047493 | 6/2003 |
| WO | WO 03/048195 | 6/2003 |
| WO | WO 03/053339 | 7/2003 |
| WO | WO 03/094951 | 11/2003 |
| WO | WO 03/094956 | 11/2003 |
| WO | WO 2004/105790 | 12/2004 |
| WO | WO 2005/005477 | 1/2005 |
| WO | WO 2005/012346 | 2/2005 |
| WO | WO 2005/012347 | 2/2005 |
| WO | WO 2005/016312 | 2/2005 |
| WO | WO 2005/047508 | 5/2005 |
| WO | WO 2005/049061 | 6/2005 |
| WO | WO 2005/055976 | 6/2005 |
| WO | WO 2005/058961 | 6/2005 |
| WO | WO 2005/092301 | 10/2005 |
| WO | WO 2006/023943 | 3/2006 |
| WO | WO 2006/079641 | 8/2006 |
| WO | WO 2006/082204 | 8/2006 |
| WO | WO 2006/082205 | 8/2006 |
| WO | WO 2006/097521 | 9/2006 |
| WO | WO 2007/006320 | 1/2007 |
| WO | WO 2007/041481 | 4/2007 |
| WO | WO 2007/047948 | 4/2007 |
| WO | WO 2007/074133 | 7/2007 |
| WO | WO 2007/081824 | 7/2007 |
| WO | WO 2007/096332 | 8/2007 |
| WO | WO 2007/096431 | 8/2007 |
| WO | WO 2007/104737 | 9/2007 |
| WO | WO 2007/128815 | 11/2007 |
| WO | WO 2007/128817 | 11/2007 |
| WO | WO 2008/015099 | 2/2008 |
| WO | WO 2008/034881 | 3/2008 |
| WO | WO 2008/132229 | 11/2008 |
| WO | WO 2008/145730 | 12/2008 |
| WO | WO 2009/010428 | 1/2009 |
| WO | WO 2009/022005 | 2/2009 |
| WO | WO 2009/022006 | 2/2009 |
| WO | 2009/115469 A1 | 9/2009 |

OTHER PUBLICATIONS

Bekerman et al., 2004, "Cyclosporin Nanoparticulate Lipospheres for Oral Administration," Journal of Pharmaceutical Sciences 93(5):1264-1270.

Bennett et al., 2003, "Insulin Inhibition of the Proteasome is Dependent on Degradation of Insulin by Insulin-Degrading Enzyme," Journal of Endocrinology 177:399-405.

Bhatnagar et al., 2006, "Molecular Variants and Derivatives of Insulin for Improved Glycemic Control in Diabetes," Progress in Biophysics and Molecular Biology 91(3):199-228.

Chin et al., 1994, "Communication to the Editor: On Protein Solubility in Organic Solvents," Biotechnology and Bioengineering 44:140-145.

Chu et al., 1992, "The A14 Position of Insulin Tolesrates Considerable Structural Alterations With Modest Effects on the Biological Behavior of the Hormone," Journal of Protein Chemistry 11(5):571-577.

Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.

Hashimoto et al., 1989, "Synthesis of Palmitoyl Derivatives of Insulin and Their Biological Activities" Pharmaceutical Research 6(2):171-176.

Havelund et al., 2004, "The Mechanism of Protraction of Insulin Detemir, a Long-Acting, Acylated Analog of Human Insulin" Pharmaceutical Research 21(8):1498-1504.

Hinds et al., 2000, "Synthesis and Characterization of Poly(Ethylene Glycol)-Insulin Conjugates," Bioconjugate Chemistry 11(2):195-201.

Hinds et al., 2002, "Effects of Peg Conjugation on Insulin Properties," Advanced Drug Delivery Reviews 54(4):505-530.

Iwamoto, 2000, "New Insulin Formulation," Annual Review Endocrine Metabolism pp. 46-53.

Jonassen et al., 2006, "Synthesis of Palmitoyl Derivatives of Insulin and Their Biological Activities," Pharmaceutical Research 23(1):49-55.

Kochendoerfer et al., 2003, "Design and Chemical Synthesis of a Homogenous Polymer-Modified Erythropoiesis Protein," Science 299:884-887.

Kurtz et al., 1983, "Circulating IgG Antibody to Protamine in Patients Treated with Protamine-Insulins," Diabetologia 25(2):322-324.

(56) References Cited

OTHER PUBLICATIONS

Markussen et al., 1987, "Soluble, Prolonged-Acting Insulin Derivatives. I. Degree of Protraction, Crystallizability of Insulins Substituted in the . . . " Protein Engineering 1(3):205-213.
Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2(2):157-166.
Muranishi et al., 1992, "Trials of Lipid Modification of Peptide Hormones for Intestinal Delivery," Journal of Controlled Release 19:179-188.
Samuel et al., 1978, "Studies on the Immunogenicity of Protamines in Humans Andexperimental Animals by Means of a Micro-Complement Fixation Test," Clinical Experminemtal Immunology 33:252-260.
Schilling et al., 1991, "Degradation of Insulin by Trypsin and Alpha Chymotrypsin," Pharmaceutical Research 8(6):721-727.
Schlichtkrull et al., 1956, "Insulin Crystals," Acta Chemica Scandinavica 10(9):1455-1458.
Seabright et al., 1996, "The Characterization of Endosomal Insulin Degradation Intermediates and Their Sequence of Production," Biochemical Journal 320(3):947-956.
Stentz et al., 1989, "Identification of Insulin Intermediates and Sites of Cleavage of Native Insulin by Insulin Protease From Human Fibroblasts," Journal of Biological Chemistry 264(34):20275-20285.
Toorisaka et al., 2004, "Emulsion-Based Drug Delivery Systems," Membrane 29(2):98-104 Abstract.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
JP 10-509176 Machine Translation Sep. 8, 1998.
JP 11-502110 Machine Translation Feb. 23, 1999.
JP 1-254699 English Abstract Oct. 11, 1989.
JP 2000-501419 Machine Translation Feb. 8, 2000.
JP 2000-504732 Machine Translation Apr. 18, 2000.
JP 2001-521004 Machine Translation Nov. 6, 2001.
JP 2001-521006 Machine Translation Nov. 6, 2001.
JP 2001-521904 Machine Translation Nov. 13, 2001.
JP 2002-308899 Machine Translation Oct. 23, 2002.
JP 2002-543092 Machine Translation Dec. 17, 2002.
JP 57-067548 English Abstract Apr. 24, 1982.
JP 9-502867 Machine Translation Mar. 25, 1997.
Non-Final Office Action mailed Jul. 12, 2010 in U.S. Appl. No. 12/560,833, filed Sep. 16, 2009 by Jonassen et al.
Notice of Abandonment mailed Jul. 23, 2010 in U.S. Appl. No. 11/814,374, filed Jan. 29, 2008 by Garibay et al.
Non-Final Office Action mailed Nov. 17, 2009 in U.S. Appl. No. 11/814,374, filed Jan. 29, 2008 by Garibay et al.
Non-Final Office Action mailed Apr. 17, 2009 in U.S. Appl. No. 11/814,374, filed Jan. 29, 2008 by Garibay et al.
Non-Final Office Action mailed Sep. 24, 2010 in U.S. Appl. No. 11/814,019, filed Oct. 4, 2007 by Kodra et al.
Advisory Action mailed Jul. 23, 2010 in U.S. Appl. No. 11/814,019, filed Oct. 4, 2007 by Kodra et al.
Final Office Action mailed Feb. 1, 2010 in U.S. Appl. No. 11/814,019, filed Oct. 4, 2007 by Kodra et al.
Non-Final Office Action mailed Jun. 18, 2009 in U.S. Appl. No. 11/814,019, filed Oct. 4, 2007 by Kodra et al.
Notice of Allowance mailed Sep. 8, 2009 in U.S. Appl. No. 11/343,005, filed Jan. 30, 2006 by Jonassen et al.
Advisory Action mailed Mar. 20, 2009 in U.S. Appl. No. 11/343,005, filed Jan. 30, 2006 by Jonassen et al.
Final Office Action mailed Dec. 24, 2008 in U.S. Appl. No. 11/343,005, filed Jan. 30, 2006 by Jonassen et al.
Non-Final Office Action mailed Jul. 11, 2008 in U.S. Appl. No. 11/343,005, filed Jan. 30, 2006 by Jonassen et al.
Notice of Allowance mailed Feb. 6, 2007 in U.S. Appl. No. 10/620,651, filed Jul. 16, 2003 by Markussen et al.
Non-Final Office Action mailed Jun. 27, 2006 in U.S. Appl. No. 10/620,651, filed Jul. 16, 2003 by Markussen et al.
Notice of Allowance mailed Apr. 9, 2003 in U.S. Appl. No. 09/861,687, filed May 21, 2001 by Markussen et al.
Non-Final Office Action mailed Sep. 27, 2002 in U.S. Appl. No. 09/861,687, filed May 21, 2001 by Markussen et al.
Notice of Allowance mailed Feb. 22, 2001 in U.S. Appl. No. 08/932,082, filed Sep. 17, 1997 by Markussen et al.
Final Office Action mailed Oct. 20, 2000 in U.S. Appl. No. 08/932,082, filed Sep. 17, 1997 by Markussen et al.
Non-Final Office Action mailed May 23, 2000 in U.S. Appl. No. 08/932,082, filed Sep. 17, 1997 by Markussen et al.
Final Office Action mailed Jun. 17, 1999 in U.S. Appl. No. 08/932,082, filed Sep. 17, 1997 by Markussen et al.
Non-Final Office Action mailed Sep. 23, 2008 in U.S. Appl. No. 08/932,082, filed Sep. 17, 1997 by Markussen et al.
Notice of Abandonment mailed Mar. 12, 1998 in U.S. Appl. No. 08/448,210, filed May 23, 1995 by Markussen et al.
Notice of Allowance mailed May 27, 1997 in U.S. Appl. No. 08/448,210, filed May 23, 1995 by Markussen et al.
Non-Final Office Action mailed May 30, 1996 in U.S. Appl. No. 08/448,210, filed May 23, 1995 by Markussen et al.
Aminlari, M. et al., Protein Dispersibility of Spray-Dried Whole Soybean Milk Base: Effect of Processing Variables, Journal of Food Science, vol. 42 (4), pp. 985-988 (1977).
Foster, T., et al., Powder Characteristics of Proteins Spray-Dried From Different Spray-Dryers, Drug Development and Industrial Pharmacy, vol. 21 (15), 1705-23 (1995).
Abstract of Chinese Patent 1390854 Granted Sep. 8, 2004.

\* cited by examiner

METHOD FOR DRYING A PROTEIN COMPOSITION, A DRIED PROTEIN COMPOSITION AND A PHARMACEUTICAL COMPOSITION COMPRISING THE DRIED PROTEIN

CROSS-REFERENCE TO RELATED APPLICATIONS

This application is a 35 U.S.C. §371 national stage application of International Patent Application PCT/EP2008/055306 (published as WO 2008/132224), filed Apr. 30, 2008, which claimed priority of European Patent Application 07107221.9, filed Apr. 30, 2007 and European Patent Application 07117798.4, filed Oct. 3, 2007; this application further claims priority under 35 U.S.C. §119 of U.S. Provisional Application 60/927,086, filed May 1, 2007 and U.S. Provisional Application 60/977,424, filed Oct. 4, 2007.

FIELD OF THE INVENTION

The present invention relates to a method for drying of protein solutions and the dried protein product. The invention also relates to pharmaceutical compositions containing such dried protein, to methods of treating diabetes and hyperglycaemia using the dried protein of the invention and to the use of such dried protein in the treatment of diabetes and hyperglycaemia.

BACKGROUND OF THE INVENTION

Drying is a mass transfer process resulting in the removal of water moisture by evaporation from a solid, semi-solid or liquid to end in a solid state.

A possible drying method is vacuum drying, where heat is supplied by contact conduction or radiation (or microwaves) while the produced vapor is removed by the vacuum system.

Another technique is drum drying, where a heated surface is used to provide the energy and aspirators draw the vapor outside the room.

Freeze drying or lyophilization is a drying method commonly used in the biochemical industry. The solvent is frozen prior to drying and is then sublimed, i.e., passed to the gas phase directly from the solid phase, below the melting point of the solvent. Freeze drying is often carried out under high vacuum to allow drying to proceed at a reasonable rate. Denaturation of protein and peptides can occur during freezing, leading to a freeze dried product with poor quality.

Spray drying has a wide range of application within the chemical industry, the food industry, and the biochemical and pharmaceutical industries. Spray drying has been used in the pharmaceutical industry since the early 1940's. It is a useful method for the processing of pharmaceuticals since it offers a means for obtaining powders with predetermined properties, such as particle size distribution and shape. In addition a number of formulation processes can be accomplished in one step in a spray dryer: these include encapsulation, complex formation and even polymerizations. Spray drying is also a convenient method of drying heat sensitive pharmaceuticals, such as protein drugs with minimal loss of activity.

The international patent application WO 00/00176 disclose a microparticle formulation obtainable by spray-drying a substantially pure solution of a therapeutic agent without the concomitant production of an undesirable high concentration of salt or other excipients. Salt is said to be undesirable because it has no stabilising effect, indeed the stability may be greater with reduced amounts of salt. Insulin microparticles are obtainable by dissolving Zn-insulin in acid (HCl), adding alkali (NaOH) to give an insulin solution, e.g. to a pH above 7, and spray-drying the insulin solution. The added Hydrochloric acid and Sodium hydroxide leaves the spray-dried microparticle formulation with a salt content. Further the obtained formulation will on addition to water have the same pH as the protein solution fed in the spray-dryer.

International patent publication WO 95/24183 relates to methods and compositions for pulmonary delivery of insulin. The insulin powders are produced by mixing bulk crystalline insulin in a sodium citrate buffer containing excipients (mannitol and/or raffinose) to give final solids concentration of 7.5 mg/ml and a pH of 6.7±0.3 and then spray-drying the insulin solution.

International patent publication WO 05/092301 relates to spray drying a clear solution of insulin at pH under the isoelectric point of insulin, preferably lower than 5.4.

Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. GLP-1 stimulates insulin secretion in a glucose-dependant manner, stimulates insulin biosynthesis, promotes beta cell rescue, decreases glucagon secretion, gastric emptying and food intake. Human GLP-1 is hydrolysed to GLP-1(7-37) and GLP-1(7-36)-amide which are both insulinotropic peptides.

The therapeutic hormone insulin is a small protein having influence on the blood glucose level. It is daily used in the medical treatment of diabetes by millions of people. Diabetes is a chronic disease caused by absolute or relative deficiency of insulin and insulin resistance, which results in high blood glucose levels (hyperglycemia) leading to long-term complications.

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of long acting insulin to cover the basal insulin requirement supplemented by bolus injections of rapid acting insulin to cover the insulin requirement related to meals.

The molecule of insulin consists of two chains, A and B, with 21 and 30 residues respectively. The A chain is built up by two helical fragments separated by a short elongated part linked to one of the helices by an intra-chain disulfide bond. Two additional disulfide bonds link the A chain to the larger B chain. In the biologically active form insulin exists as a monomer in which the B chain contains a central helical region flanked by two elongated parts. In the presence of divalent ions like zinc, the monomers assemble into hexamers, where each of the two central zinc ions is coordinated by three histidine residues.

Insulin is susceptible to fibrillation, a misfolding process leading to well ordered cross-β assembly. Protection from fibrillation in βcells is provided by sequestration of the susceptible monomer within zinc hexamers. When fibrillation occurs during the spray-drying of insulin, the nozzle may clog, leading to interruptions in the drying process.

Another important factor when avoiding clogging of the spray-drying nozzles is that the protein to be dried is properly dissolved in the solution. Protein dispersed in the feed solution may also lead to clogging of the equipment.

Further the pH of the dried protein is very important. It is often desirable to obtain a dried product with a specified pH, eg. a pH comparable to physiological pH.

SUMMARY OF THE INVENTION

The present invention concerns a process for drying a protein solution, wherein
a) A protein solution is obtained by mixing a protein with water optionally comprising excipients and adjusting the pH with a volatile base, a non volatile base and optionally a non volatile acid for the protein solution to become alkaline, and
b) Drying the protein solution Additionally the invention concerns a dried protein obtainable by the mentioned process, a pharmaceutical composition comprising the dried protein and a method for treating diabetes.

DEFINITIONS

A "protein solution" as mentioned herein means a solution of insulin, insulin analogues, insulin derivatives, GLP-1, GLP-1 analogues, GLP-1 derivatives or glucagon which has been solubilised without the use of acids and at pH values above the isoelectric point of the protein.

By "volatile base" is meant a base, which to some extend will evaporate upon heating and/or at reduced pressure, e.g. bases which have a vapour pressure above 65 Pa at room temperature or an aqueous azeotropic mixture including a base having a vapour pressure above 65 Pa at room temperature.

A "non volatile base" as mentioned herein means a base, which do not evaporate or only partly evaporate upon heating, e.g. bases with a vapour pressure below 65 Pa at room temperature.

A "non volatile acid" as mentioned herein means an acid, which do not evaporate or only partly evaporate upon heating, e.g. acids with a vapour pressure below 65 Pa at room temperature such as phosphoric acid.

A "strong acid" as mentioned herein means an acid, which have a pKa value below −1 such as hydrochloric acid and sulphuric acid.

With "insulin" as used herein is meant human insulin, porcine insulin or bovine insulin with disulfide bridges between CysA7 and CysB7 and between CysA20 and CysB19 and an internal disulfide bridge between CysA6 and CysA11 or an insulin analogue or derivative thereof.

With "GLP-1" as used herein is meant glucagon-like peptide-1. Human GLP-1 is a 37 amino acid residue peptide. Human GLP-1 is hydrolysed to GLP-1(7-37) and GLP-1(7-36)-amide which are both insulinotropic peptides.

By "pH of the protein solution/insulin solution/GLP-1 solution/glucagon solution" is meant the pH of the protein/insulin/GLP-1/glucagon solution after adjustment with volatile and non volatile bases and before spray drying of the protein solution.

By "pH of the dried protein/insulin/GLP-1/glucagon" is meant the pH of the dried/spray-dried protein/insulin/GLP-1/glucagon when mixing at least 20 mg spray dried/dried protein with 0.5 ml demineralised water, giving a concentration of at least 40 mg protein/insulin/GLP-1 per ml of demineralised water, and measuring pH. The pH of the dried protein/insulin/GLP-1 can be measured by mixing up to about 300 mg spray dried/dried protein/insulin/GLP-1 with 0.5 ml demineralised water and measuring the pH. For example the pH is measure by mixing about 20 to about 250 mg spray dried/dried protein/insulin/GLP-1/glucagon with 0.5 ml demineralised water, by mixing about 20 to about 200 mg spray dried/dried protein/insulin/GLP-1/glucagon with 0.5 ml demineralised water, by mixing about 20 to about 150 mg spray dried/dried protein/insulin/GLP-1/glucagon with 0.5 ml demineralised water or by mixing about 20 to about 100 mg spray dried/dried protein/insulin/GLP-1/glucagon with 0.5 ml demineralised water and measuring pH.

By "target pH for the dried protein" is meant the pH for the dried protein/insulin/GLP-1/glucagon that are desirable to achieve for the dried protein, eg. the pH where the chemical stability of the dried protein is optimal or the pH of the dried protein is comparable to physiological pH.

By "target pH for the protein solution" is meant the pH that would be desirable for the protein solution/insulin solution/GLP-1 solution/glucagon solution when it should be dried, eg. the pH are at the optimum for the dissolved protein due to high solubility or low aggregaton potential.

By "analogue" as used herein is meant a polypeptide which has a molecular structure which formally can be derived from the structure of the protein, by deleting and/or exchanging at least one amino acid residue occurring in the naturally occurring protein and/or adding at least one amino acid residue. The added and/or exchanged amino acid residues can either be codable amino acid residues or other naturally occurring residues or purely synthetic amino acid residues. The insulin analogues may be such wherein position 28 of the B chain may be modified from the natural Pro residue to one of Asp, Lys, or Ile. In another aspect Lys at position B29 of insulin is modified to Pro or Glu. Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys, Thr, Ser, Gln, Glu or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

A simple system is used to describe analogues of the GLP-1 peptide. Thus, for example, $[Gly^8]GLP-1(7-37)$ designates an analogue of GLP-1(7-37) formally derived from GLP-1(7-37) by substituting the naturally occurring amino acid residue in position 8 (Ala) by Gly. The GLP-1 analogues may be such wherein the naturally occurring Lys at position 34 of GLP-1(7-37) has been substituted with Arg. All amino acids for which the optical isomer is not stated is to be understood to mean the L-isomer.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

With "desB30 insulin", "desB30 human insulin" is meant insulin or an analogue thereof lacking the B30 amino acid residue.

By "parent insulin" is meant a naturally occurring insulin such as human insulin or porcine insulin. Alternatively, the parent insulin can be an insulin analogue.

By "derivative" as used herein is meant a naturally occurring protein or an analogue thereof which has been chemically modified, e.g. by introducing a substituent in one or more positions of the protein backbone or by oxidizing or reducing groups of the amino acid residues in the protein or by acylating a free amino group or a hydroxy group.

DESCRIPTION OF THE INVENTION

With the process of the invention it is possible to obtain a dried protein powder with a pH that is different from the pH of the protein solution which are dried.

The present invention concerns process for drying a process for drying a protein solution, wherein
  a) A protein solution is obtained by mixing a protein with water optionally comprising excipients and adjusting the pH with a volatile base, a non volatile base and optionally a non volatile acid for the protein solution to become alkaline, and
  b) Drying the protein solution.

In one aspect of the invention the process comprises:
  a) Selecting a target pH for the dried protein,
  b) Selecting a target pH for the protein solution,
  c) Providing an aqueous phase,
  d) Adding a protein,
  e) Optionally adding excipients,
  f) Adjusting the pH with a non volatile base and optionally a non volatile acid to the target pH for the dried protein,
  g) Adjusting the pH with a volatile base to the target pH of the protein solution to be dried, and
  h) Spray-drying the protein solution.
wherein the steps d, e, f and g can be carried out in any order while stirring continuously.

In one aspect of the invention the steps d, e and f can be carried out in any order while stirring continuously.

In one aspect the protein solution is adjusted with a volatile base and a non volatile base. In one aspect the process the protein solution is obtained at a temperature below about 8° C., below about 6° C., below about 5° C., below about 4° C., below about 3° C., below about 2° C. or below about 1° C.

In one aspect the freezing point of the water is depressed and protein solution is obtained at a temperature below 0° C.

In one aspect the protein solution has a pH or a target pH above about 7.4, above about 7.6, above about 7.8, above about 8.0, above about 8.2, above about 8.4 or above about 8.6. The tendency for the proteins to fibrillate is less pronounced when the pH of the protein solution is between about 7.6 and about 11.0, between about 7.6 and about 10.5, between about 7.8 and about 11.0, between about 7.8 and about 10.5, between about 8.0 and about 11.0, between about 8.0 and about 10.5, between about 8.2 and about 11.0, between about 8.4 and about 11.0, between about 8.6 and about 10.0, between about 8.8 and about 10.0, between about 9.0 and about 10.0 or between about 9.2 and about 10.0.

In one aspect of the invention the protein is added to an aqueous solution. The aqueous solution can be pure water or it can contain excipients or an alkaline.

In one aspect of the invention the pH of the protein solution is adjusted with an alkaline solution comprising a non volatile base. The non volatile base can be selected from the group consisting of alkaline metal salts, alkaline metal hydroxides, alkaline earth metal salts, alkaline earth metal hydroxides and amino acids or a combination hereof. For example the pH can be adjusted with sodium hydroxide, potassium hydroxide, calcium hydroxide, calcium oxide or any combination hereof.

In one aspect of the invention the pH of the protein solution is adjusted with an alkaline solution comprising a volatile base. The volatile base can be selected from the group consisting of ammonium hydroxides, tetraalkylammonium hydroxides, secondary amines, tertiary amines, aryl amines, alphatic amines or ammonium bicarbonate or a combination. For example the volatile base can be bicarbonate, carbonate, ammonia, hydrazine or an organic base such as a lower aliphatic amines e.g. trimethyl amine, triethylamine, diethanolamines, triethanolamine and their salts. Further the volatile base can be ammonium hydroxide, ethyl amine or methyl amine or a combination hereof.

Upon addition of ammonium hydroxide to an aqueous solution containing insulin, the protein, for example insulin will dissolve more rapidly.

In one aspect of the invention the pH of the protein solution is adjusted with an alkaline solution comprising a volatile base and a non volatile base. In one aspect the pH of the protein solution is adjusted with sodium hydroxide to the target pH for the dried protein and with ammonium hydroxide to obtain the selected pH for the protein solution to be spray-dried.

In one aspect of the invention, the volatile base is used to adjusts the pH of the protein solution with at least about 0.5 pH unit, at least about 0.7 pH unit, or at least about 0.9 pH unit or at least about 1.1 pH unit, or at least about 1.3 pH unit or at least about 1.5 pH unit.

In solution, the self-association pattern of insulin is a complex function of protein concentration, metal ions, pH, ionic strength and solvent composition. For some of the currently used solutions containing insulin, zinc ions, salts and phenolic compounds, the following equilibria must be considered:

$6In \leftrightarrow 3In_2$

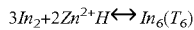

$3In_2 + 2Zn^{2+} H \leftrightarrow In_6(T_6)$

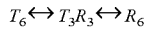

$T_6 \leftrightarrow T_3R_3 \leftrightarrow R_6$ where In is insulin, $In_2$ is dimeric insulin, $In_6$ is hexameric insulin, $T_6$ is hexameric insulin in the $T_6$ conformation, $T_3R_3$ is hexameric insulin in the $T_3R_3$ conformation and $R_6$ is hexameric insulin In the hexameric $R_6$ state.

The known degradation patterns of insulin include a) fibril formation; b) deamidations at A18, A21 and B3; c) dimerisations via transamidation or Schiff-base formation; d) disulfide exchange reactions.

According to Brange (Stability of Insulin, Kluwer Academic Press, 1994), each of these degradation reactions proceed much faster in the monomeric state than in the hexameric state. Therefore, the most efficient means of stabilising insulin preparations is by pushing the above equilibrium as far to the right as possible. In addition to this general effect of mass action, the reactivity of selected residues is further modified depending on their direct involvement in the T→R conformational change. Thus, the reactivity of B3Asn is much lower in the R-state (when the residue resides in an alfa-helix) than in the T-state.

The interconversion between $T_6$, $T_3R_3$ and $R_6$ conformations of the two zinc insulin hexamer is modulated by ligand binding to the $T_3R_3$ and $R_6$ forms. Anions such as chloride have affinity for the fourth coordination position in the metal ions of $T_3R_3$ and $R_6$, while preservatives such as phenol binds to hydrophobic pockets located near the surfaces of the $T_3R_3$ and $R_6$ forms (Derewenda, Nature and, Brzovic, Biochemistry 33, 130557, 1994).

Therefore, conditions which favour the $R_6$ conformation of insulin in solution are an advantage both during the drying process in order to avoid denaturation of insulin and during shelf storage in order to maximise the chemical stability.

In one aspect of the invention the protein solution comprises phenol. In one aspect the protein solution comprises at least about 2 moles of phenol per mole of protein, or at least about 3 moles of phenol per mole of protein or at least about 4 moles of phenol per mole of protein. In one aspect the protein solution comprises about 4 moles of phenol per mole of insulin. In one aspect the protein solution comprises about 4 moles of phenol per mole of insulin and the protein solution comprises zinc. When the protein solution comprises insulin, the phenol stabilises the insulin hexamer.

In one aspect of the invention the protein is selected from the group consisting of insulin, insulin analogues, insulin derivatives, GLP-1, GLP-1 analogues and GLP-1 derivatives, glucagon and/or any combination thereof.

In one aspect of the invention the protein solution comprises a protein selected from the group consisting of insulin, insulin analogues, insulin derivatives and the solution further comprises zinc. The zinc content of the protein solution comprising insulin can be in the range of about 2 to about 4 zinc ions per insulin hexamer, or the zinc content can be in the range of about 2.1 to about 3 zinc ions per insulin hexamer or the zinc content can be in the range of about 2.2 to about 2.7 zinc ions per insulin hexamer. The zinc content of the protein solution comprising insulin can be about 2.3 zinc ions per insulin hexamer.

In one aspect of the invention the protein solution comprises a buffer, a detergent, a stabilizer, a protease inhibitor, a flavour, a carrier, an absorption protecting agent, a bulking agent or an agent improving the flowing properties or a penetration enhancer.

In one aspect of the invention the protein solution comprises glycylglycine. When glycylglycine is added to a protein solution, the protein dissolves more rapidly. In one aspect glycylglycine is added to an aqueous solution comprising insulin. The concentration of glycylglycine in the solution will be between about 4 mM and about 200 mM.

In one aspect of the invention the method for drying or spray-drying a protein solution a target pH for the dried protein is determined. The pH of the protein solution to be dried or spray-dried is above the target pH of the dried protein. The pH of the protein solution may be at least about 0.5 pH units above the pH of the dried protein. The pH of the protein solution may be at least about 0.7, at least about 0.9, at least about 1.1, at least about 1.3 or at least about 1.5, or at least about 2.0, or at least about 2.5 pH units above the pH of the of the spray-dried protein.

In one aspect of the invention the pH or the target pH of the spray dried protein is between about 6.0 and about 8.5, between about 6.2 and about 8.4, between about 6.4 and about 8.3, between about 6.6 and about 8.2, between about 6.8 and about 8.1, between about 7.0 and about 8.0, between about 7.2 and about 7.9, between about 7.4 and about 7.8 or between about 7.6 and about 7.7.

In one aspect of the invention the protein solution is dried or spray dried to obtain a water content below about 10%. The water content may be below about 6%, below about 4%, below about 2% or below about 1% calculated on/measured by loss on drying test (gravimetric) as stated in the experimental part.

In one aspect of the invention the protein to be dried or spray-dried is selected from the group consisting of AspB28 human insulin; LysB28ProB29 human insulin and LysB3GluB29 human insulin.

In one aspect the invention relates to a dried protein obtainable by the inventive process.

In one aspect the invention relates to a dried protein as described in the examples.

In one aspect of the invention is related to a pharmaceutical composition comprising a therapeutically effective amount of a dried protein, such as insulin, insulin analogues, insulin derivatives, GLP-1, GLP-1 analogues, GLP-1 derivatives, glucagon and/or any combination thereof according to the invention, which composition can be provided for the treatment of type 1 diabetes, type 2 diabetes and other states that cause hyperglycaemia in patients in need of such a treatment.

In one aspect the invention is related to a pharmaceutical composition comprising a therapeutically effective amount of a dried protein, such as insulin, insulin analogues, insulin derivatives, GLP-1, GLP-1 analogues, GLP-1 derivatives, glucagon and/or any combination thereof together with a pharmaceutically acceptable carrier and/or a pharmaceutically acceptable additive, which composition can be provided for the treatment of type 1 diabetes, type 2 diabetes and other states that cause hyperglycaemia in patients in need of such a treatment.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the dried protein according to the invention, such as insulin, insulin analogues, insulin derivatives, GLP-1, GLP-1 analogues, GLP-1 derivatives, glucagon and/or any combination thereof.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the dried protein according to the invention, such as insulin, insulin analogues, insulin derivatives, GLP-1, GLP-1 analogues, GLP-1 derivatives, glucagon and/or any combination thereof, optionally together with a pharmaceutically acceptable carrier and/or pharmaceutical acceptable additives.

In one aspect of the invention, there is provided a pharmaceutical composition for treating type 1 diabetes, type 2 diabetes and other states that cause hyperglycaemia in a patient in need of such a treatment, the composition comprising a therapeutically effective amount of a dried protein according to the invention, such as insulin, insulin analogues, insulin derivatives, GLP-1, GLP-1 analogues, GLP-1 derivatives, glucagon in mixture with one or two spray-dried proteins according to the invention, such as insulin, insulin analogues, insulin derivatives, GLP-1, GLP-1 analogues, GLP-1 derivatives, glucagon optionally together with pharmaceutically acceptable carriers and/or additives.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising a dried protein according to the invention, such as insulin, insulin analogues, insulin derivatives, GLP-1, GLP-1 analogues, GLP-1 derivatives, glucagon in mixture with one or two dried proteins according to the invention, such as insulin, insulin analogues, insulin derivatives, GLP-1, GLP-1 analogues, GLP-1 derivatives, glucagon optionally together with a pharmaceutically acceptable carrier and/or pharmaceutical acceptable additives.

One aspect of the invention is related to a pharmaceutical composition comprising a therapeutically effective amount of a dried protein according to the invention, such as insulin, insulin analogues, insulin derivatives, GLP-1, GLP-1 analogues, GLP-1 derivatives, glucagon and/or any combination thereof, optionally together with a pharmaceutically acceptable carrier and/or a pharmaceutically acceptable additive, which can be provided for pulmonary treatment of type 1 diabetes, type 2 diabetes and other states that cause hyperglycaemia in patients in need of such a treatment.

In one aspect the invention is related to application of a pharmaceutical composition for pulmonary treatment of type 1 diabetes, type 2 diabetes and other states that cause hyperglycaemia in a patient in need of such a treatment, the pharmaceutical composition comprising a therapeutically effective amount of a dried protein according to the invention, such as insulin, insulin analogues, insulin derivatives, GLP-1, GLP-1 analogues, GLP-1 derivatives, glucagon and/or any combination thereof, optionally in mixture with an insulin or an insulin analogue which has a rapid onset of action, together with pharmaceutically acceptable carriers and/or additives.

In one aspect of the invention, there is provided a method for the manufacture of a pharmaceutical composition for the use in the treatment of type 1 diabetes, type 2 diabetes and other states that cause hyperglycaemia, the composition being used pulmonary and comprising a therapeutically effective amount of a dried protein according to the invention, such as insulin, insulin analogues, insulin derivatives, GLP-1, GLP-1 analogues, GLP-1 derivatives, glucagon and/or any combination thereof, optionally in mixture with an insulin or an insulin analogue which has a rapid onset of action, together with a pharmaceutically acceptable carrier and/or pharmaceutical acceptable additives.

Production of Insulin

The insulin or a precursor thereof can be produced by either well-know peptide synthesis or by well known recombinant production in suitable transformed microorganisms. Thus the insulin can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

When preparing the insulin derivatives to be used in the pharmaceutical formulation according to the invention, the starting product for the substitution, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture. Reference is made to international patent application WO 2005/012347.

Pharmaceutical Compositions

The dried protein of this invention can, for example, be administered subcutaneously, orally, nasally or pulmonary.

For subcutaneous administration, the dried insulin is formulated analogously with the formulation of known insulin. Furthermore, for subcutaneous administration, the dried insulin of this invention is administered analogously with the administration of known insulin and, generally, the physicians are familiar with this procedure.

The dried insulin of this invention may be administered by inhalation in a dose effective manner to increase circulating insulin levels and/or to lower circulating glucose levels. Such administration can be effective for treating disorders such as diabetes or hyperglycaemia. Achieving effective doses of insulin requires administration of an inhaled dose of dried insulin of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

According to the invention, dried insulin of this invention may be delivered by inhalation to achieve rapid absorption thereof. Administration by inhalation can result in pharmacokinetics comparable to subcutaneous administration of insulin. Inhalation of dried insulin of this invention leads to a rapid rise in the level of circulating insulin followed by a rapid fall in blood glucose levels. Different inhalation devices typically provide similar pharmacokinetics when similar particle sizes and similar levels of lung deposition are compared.

According to the invention, dried insulin of this invention may be delivered by any of a variety of inhalation devices known in the art for administration of a therapeutic agent by inhalation. These devices include metered dose inhalers, nebulizers, dry powder generators, sprayers, and the like dried insulin of this invention is delivered by a dry powder inhaler or a sprayer. There are a several desirable features of an inhalation device for administering dried insulin of this invention. For example, delivery by the inhalation device is advantageously reliable, reproducible, and accurate. The inhalation device should deliver small particles, for example particles less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of dried protein of the invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of dried insulin of this invention in a given quantity of the powder determines the dose delivered in a single administration.

The particle size of dried insulin of this invention in the formulation delivered by the inhalation device is critical with respect to the ability of insulin to make it into the lungs, and into the lower airways or alveoli. The dried insulin of this invention can be formulated so that at least about 10% of the insulin conjugate delivered is deposited in the lung, for example about 10 to about 20%, or more. It is known that the maximum efficiency of pulmonary deposition for mouth breathing humans is obtained with particle sizes of about 2 µm to about 3 µm. Pulmonary deposition decreases substantially when particle sizes are above about 5 µm. Particle sizes below about 1 µm cause pulmonary deposition to decrease, and it becomes difficult to deliver particles with sufficient mass to be therapeutically effective. Thus, particles of dried protein delivered by inhalation have a particle size less than about 10 μm, for example in the range of about 1 μm to about 5 μm. The formulation of dried protein is selected to yield the desired particle size in the chosen inhalation device.

Advantageously for administration as a dry powder, dried protein of this invention is prepared in a particulate form with a particle size of less than about 10 μm, for example about 1 to about 5 μm. The particle size is effective for delivery to the alveoli of the patient's lung. The dry powder is largely composed of particles produced so that a majority of the particles have a size in the desired range. Advantageously, at least about 50% of the dry powder is made of particles having a diameter less than about 10 μm.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of dried protein of this invention for administration from a dry powder inhaler typically include a finely divided dry powder containing the dried protein, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The dried protein can be mixed with an additive at a molecular level or the solid formulation can include particles of the protein conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 99% by weight of the formulation. Additional agents known in the art for formulation of a protein such as insulin analogue protein can also be included in the formulation.

The protein solution may optionally be combined with pharmaceutical carriers or excipients which are suitable for respiratory and pulmonary administration. Such carriers may serve simply as bulking agents when it is desired to reduce the insulin concentration in the powder which is being delivered to a patient, but may also serve to enhance the stability of the insulin compositions and to improve the dispersability of the powder within a powder dispersion device in order to provide more efficient and reproducible delivery of the insulin and to improve handling characteristics of the insulin such as flowability and consistency to facilitate manufacturing and powder filling.

Suitable carrier materials may be in the form of an amorphous powder, a crystalline powder, or a combination of amorphous and crystalline powders. Suitable materials include carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins, such as aspartame, human serum albumin, gelatin, and the like; (e) alditols, such as mannitol, xylitol, and the like. A preferred group of carriers includes lactose, trehalose, raffinose, maltodextrins, glycine, sodium citrate, tromethamine hydrochloride, human serum albumin, and mannitol.

Such carrier materials may be combined with the insulin prior to spray drying, i.e., by adding the carrier material to the protein solution or the aqueous which is prepared for spray drying. In that way, the carrier material will be formed simultaneously with and as part of the protein particles.

Typically, when the carrier is formed by spray drying together with the protein, the protein will be present in each individual particle at a weight percent in the range from 5% to 95%, preferably from 20% to 80%. The remainder of the particle will primarily be carrier material (typically being from 5% to 95%, usually being from 20% to 80% by weight), but will also include buffer (s) may include other components as described above.

Alternatively, the carriers may be separately prepared in a dry powder form and combined with the dry powder protein by blending. The separately prepared powder carriers will usually be crystalline (to avoid water absorption), but might in some cases be amorphous or mixtures of crystalline and amorphous. The size of the carrier particles may be selected to improve the flowability of the insulin powder, typically being in the range from 25 m to 100 m. Carrier particles in this size range will generally not penetrate into the alveolar region of the lung and will often separate from the insulin in the delivery device prior to inhalation. Thus, the particles which penetrate into the alveolar region of the lung will consist essentially of insulin and buffer. A preferred carrier material is crystalline mannitol having a size in the above-stated range.

The dry insulin powders of the present inventions may also be combined with other active components. For example, it may be desirable to combine small amounts of amylin or active amylin analogues in the insulin powders to improve the treatment of diabetes. Amylin is a hormone which is secreted with insulin from the pancreatic 0-cells in normal (non-diabetic) individuals. It is believed that amylin modulates insulin activity in vivo, and it has been proposed that simultaneous administration of amylin with insulin could improve blood glucose control. Combining dry powder amylin with insulin in the compositions of the present invention will provide a particularly convenient product for achieving such simultaneous administration. Amylin may be combined with insulin at from 0.1% by weight to 10% by weight (based on the total weight of insulin in a dose), preferably from 0.5% by weight to 2.5% by weight. Amylin is available from commercial suppliers, such as Amylin Corporation, San Diego, Calif., and can be readily formulated in the compositions of the present invention. For example, amylin may be dissolved in aqueous or other suitable solutions together with the insulin, and optionally carriers, and the solution spray dried to produce the powder product.

A spray including the dried protein of this invention can be produced by forcing a suspension or solution of protein conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 µm, for example in the range of about 1 µm to about 5 µm.

Formulations of dried protein of this invention suitable for use with a sprayer will typically include proteins in an aqueous solution at a concentration of about 1 mg to about 20 mg of protein conjugate per ml of solution. The formulation can include agents such as an excipient, a buffer, an isotonicity agent, a preservative, a surfactant, and, for example zinc. The formulation can also include an excipient or agent for stabilization of the crystals, such as a buffer, a reducing agent, a bulk protein, or a carbohydrate. Bulk proteins useful in formulating dried protein conjugates include albumin, protamine, or the like. Typical carbohydrates useful in formulating protein conjugates include sucrose, mannitol, lactose, trehalose, glucose, or the like. The crystal formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing a dried protein according to the present invention may also be administered nasally. The pharmaceutical composition may be administered as a liquid composition, a dry composition or a gel. For drug delivery via the nose the crystals may be above 10 µm in order to secure deposition in the nasal cavity and to avoid that the particles are carried further down to the tracheobronchial and pulmonary region. There is no clear understanding of a upper size limit, but there probably is an upper particle size above which particles for a number of reasons will not demonstrate efficacy and maybe even could lead to local irritation.

Pharmaceutical compositions containing a dried protein according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the dried protein of the invention can be prepared using the conventional techniques of the pharmaceutical industry which involve dissolving and mixing the ingredients as appropriate to give the desired end product. Thus, according to one procedure, a crystal comprising insulin according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy*, 19$^{th}$ edition, 1995.

In a further aspect of the invention the formulation further comprises an isotonic agent which may be selected from the group consisting of a salt (e.g. sodium chloride), a sugar or sugar alcohol, an amino acid (e.g. glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

Compositions containing dried protein of this invention, such as insulin, insulin analogues, insulin derivatives, GLP-1, GLP-1 analogues, GLP-1 derivatives, glucagon can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin employed, the age, body weight, physical activity, and diet of the patient, on a possible combination with other drugs, and on the severity of the state to be treated. It is recommended that the daily dosage of the dried protein of this invention be determined for each individual patient by those skilled in the art in a similar way as for known pharmaceutical compositions.

Where expedient, the dried protein of this invention may be used in mixture with other types of proteins, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention will be summarised in the following paragraphs:

1. A process for drying a protein solution, wherein
    a) a protein solution is obtained by mixing a protein with water optionally comprising excipients and adjusting the pH with a volatile base, a non volatile base and optionally a non volatile acid for the protein solution to become alkaline, and
    b) drying the protein solution
2. A process according to paragraph 1 comprising:
    a) Selecting a target pH for the dried protein,
    b) Selecting a target pH for the protein solution,
    c) Providing an aqueous phase,
    d) Adding a protein,
    e) Optionally adding excipients,
    f) Adjusting the pH with a non volatile base and optionally a non volatile acid to the target pH for the dried protein,
    g) Adjusting the pH with a volatile base to the target pH of the protein solution to be dried, and
    h) Spray-drying the protein solution.
    wherein the steps d, e, f and g can be carried out in any order while stirring continuously.
3. A process according to paragraph 2, wherein the steps d, e and f can be carried out in any order while stirring continuously.
4. The process according to paragraphs 1-3, wherein the protein solution is obtained at a temperature below 8° C.
5. The process according to paragraphs 1-4, wherein the protein solution is obtained at a temperature below 6° C., below 5° C., below 4° C., below 3° C., below 2° C. or below 1° C.
6. The process according to paragraphs 1-5, wherein the freezing point of the aqueous phase is depressed and a protein solution is obtained at a temperature below 0° C.
7. The process according to paragraphs 1-6, wherein the drying method is selected from the group consisting of spray drying, spray freeze drying, fluid bed drying, freeze drying and vacuum drying.
8. The process according to paragraphs 1-7, wherein the protein solution has a pH above 7.4.
9. The process according to paragraphs 1-8, wherein the protein solution has a pH above 7.6, above 7.8, above 8.0, above 8.2, above 8.4 or above 8.6.
10. The process according to paragraphs 1-8, wherein the protein solution has a pH between 7.4 and 11.0.
11. The process according to paragraphs 1-8 and 10, wherein the protein solution has a pH between about 7.6 and about 11.0, between about 7.6 and about 10.5, between about 7.8 and about 11.0, between about 7.8 and about 10.5, between about 8.0 and about 11.0, between about 8.0 and about 10.5, between about 8.2 and about 11.0, between about 8.4 and about 11.0, between about 8.6 and about 10.0, between about 8.8 and about 10.0, between about 9.0 and about 10.0 or between about 9.2 and about 10.0.
12. The process according to paragraphs 1-11, wherein the non volatile base is selected from the group consisting of alkaline metal salts, alkaline metal hydroxides, alkaline earth metal salts, alkaline earth metal hydroxides and amino acids or a combination hereof.
13. The process according to paragraph 12, wherein the non volatile base is sodium hydroxide, potassium hydroxide, calcium hydroxide, calcium oxide or any combination hereof.
14. The process according to paragraphs 1-13, wherein the volatile base is selected from the group consisting of ammonium hydroxides, tetraalkylammonium hydroxides, secondary amines, tertiary amines, aryl amines, aliphatic amines or ammonium bicarbonate or a combination hereof.
15. The process according to paragraph 14, wherein the volatile base is ammonium hydroxide, ethyl amine or methyl amine or a combination hereof.
16. The process according to paragraphs 1-15, wherein the volatile base adjusts the pH of the protein solution with at least 0.5 pH unit.
17. The process according to paragraphs 1-16, wherein the volatile base adjusts the pH of the protein solution with at least 0.7 pH unit, or at least 0.9 pH unit or at least 1.1 pH unit, or at least 1.3 pH unit or at least 1.5 pH unit.
18. The process according to paragraphs 1-17, wherein the pH of the protein solution is adjusted with a solution comprising sodium hydroxide and ammonium hydroxide.
19. The process according to paragraphs 1-18, wherein the protein is selected from the group consisting of insulin, insulin analogues, insulin derivatives, GLP-1, GLP-1 analogues and GLP-1 derivatives, glucagon and/or any combination thereof.
20. The process according to paragraphs 1-19, wherein the protein solution comprises a protein selected from the group consisting of insulin, insulin analogues, insulin derivatives and the solution further comprises zinc.
21. The process according to paragraph 20, wherein the protein solution comprises phenol.
22. The process according to paragraphs 20-21, where in the protein solution comprises about 4 moles of phenol per mole of protein.
23. The process according to paragraphs 1-22, wherein the protein solution comprises a buffer, a detergent, a stabilizer, a protease inhibitor, a flavour, a carrier, an absorption protacting agent, a bulking agent or an agent improving the flowing properties or a penetration enhancer or a combination hereof
24. The process according to paragraph 23, wherein the protein solution comprises glycylglycine
25. The process according to paragraphs 1-24, wherein the pH of the protein solution is above the pH of the dried protein.
26. The process according to paragraph 25, wherein the pH of the protein solution is at least 0.5 pH units above the pH of the dried protein.
27. The process according to paragraphs 1-26, wherein the pH of the protein solution is at least 0.7, at least 0.9, at least 1.1, at least 1.3 or at least 1.5 pH units above the pH of the of the dried protein.
28. The process according to paragraphs 1-27, wherein the pH of the dried protein is between about 6.0 and about 8.5.
29. The process according to paragraphs 1-28, wherein the pH of the dried protein is between about 6.2 and about 8.4, between about 6.4 and about 8.3, between about 6.6 and about 8.2, between about 6.8 and about 8.1, between about 7.0 and about 8.0, between about 7.2 and about 7.9, between about 7.4 and about 7.8 or between about 7.6 and about 7.7.
30. The process according to paragraphs 1-29, wherein the protein solution is dried to obtain a water content of the spray dried protein below about 10%, below about 6%, below about 4%, below about 2% or below about 1%.
31. The process according to paragraphs 1-30, wherein the protein is an insulin analogue is selected from the group consisting of AspB28 human insulin; LysB28ProB29 human insulin and LysB3GluB29 human insulin.
32. Dried protein obtainable by the process of paragraphs 1-31.
33. Pharmaceutical composition comprising a therapeutically effective amount of a spray-dried protein according to paragraph 32.
34. Pharmaceutical composition according to paragraph 33 wherein the composition is for pulmonary, parenteral, nasal or oral treatment of diabetes or hyperglycaemia.
35. Pharmaceutical composition for the treatment of diabetes or hyperglycaemia in a patient in need of such treatment, comprising a therapeutically effective amount of a dried protein according to paragraph 32, wherein the protein is selected from the group consisting of insulin, insulin analogues, insulin derivatives, GLP-1, GLP-1 analogues, GLP-1 derivatives, glucagon and/or any combination thereof.
36. A method of treating diabetes in a patient in need of such a treatment, comprising administering to the patient a therapeutically effective amount of a dried protein according to any of the paragraph 32 or a pharmaceutical composition according to paragraphs 33-35.
37. A method according to paragraph 36, wherein the protein is selected from the group consisting of insulin, insulin analogues, insulin derivatives, GLP-1, GLP-1 analogues, GLP-1 derivatives, glucagon and/or any combination thereof 38. Dried protein as described in the examples.
1a. A process for drying an protein solution, wherein
   a) A protein solution is obtained by mixing a protein with water optionally comprising excipients and adjusting the pH to become alkaline, and
   b) Drying the protein solution.
2a. A process for producing a dried protein from a protein solution comprising:
   a) Selecting a target pH for the dried protein,
   b) Selecting a target pH for the protein solution,
   c) Providing an aqueous phase,
   d) Adding a protein,
   e) Optionally adding excipients,
   f) Adjusting the pH with a non volatile base to the target pH for the dried protein,
   g) Adjusting the pH with a volatile base to the target pH of the protein solution to be dried, and
   h) Spray-drying the protein solution.
   wherein the steps d, e, f and g can be carried out in any order while stirring continuously.
3a. The process according to paragraph 1a, wherein the protein solution is adjusted with a volatile base and a non volatile base.
4a. The process according to paragraphs 1a-3a, wherein the protein solution is obtained at a temperature below 8° C.
5a. The process according to paragraphs 1a-4a, wherein the protein solution is obtained at a temperature below 6° C., below 5° C., below 4° C., below 3° C., below 2° C. or below 1° C.
6a. The process according to paragraphs 1a-5a, wherein the freezing point of the aqueous phase is depressed and a protein solution is obtained at a temperature below 0° C.
7a. The process according to paragraphs 1a-6a, wherein the drying method is selected from the group consisting of spray drying, spray freeze drying, fluid bed drying, freeze drying and vacuum drying.
8a. The process according to paragraphs 1a-7a, wherein the protein solution has a pH above 7.4.
9a. The process according to paragraphs 1a-8a, wherein the protein solution has a pH above 7.6, above 7.8, above 8.0, above 8.2, above 8.4 or above 8.6.
10a. The process according to paragraphs 1a-8a, wherein the protein solution has a pH between 7.4 and 11.0.
11a. The process according to paragraphs 1a-8a and 10a, wherein the protein solution has a pH between about 7.6 and about 11.0, between about 7.6 and about 10.5, between about 7.8 and about 11.0, between about 7.8 and about 10.5, between about 8.0 and about 11.0, between about 8.0 and about 10.5, between about 8.2 and about 11.0, between about 8.4 and about 11.0, between about 8.6 and about 10.0, between about 8.8 and about 10.0, between about 9.0 and about 10.0 or between about 9.2 and about 10.0.
12a. The process according to paragraphs 1a-11a, wherein the non volatile base is selected from the group consisting of alkaline metal salts, alkaline metal hydroxides, alkaline earth metal salts, alkaline earth metal hydroxides and amino acids or a combination hereof.
13a. The process according to paragraph 12a, wherein the non volatile base is sodium hydroxide, potassium hydroxide, calcium hydroxide, calcium oxide or any combination hereof.
14a. The process according to paragraphs 1a-11a, wherein the volatile base is selected from the group consisting of ammonium hydroxides, tetraalkylammonium hydroxides, secondary amines, tertiary amines, aryl amines, aliphatic amines or ammonium bicarbonate or a combination hereof.

15a. The process according to paragraph 14a, wherein the volatile base is ammonium hydroxide, ethyl amine or methyl amine or a combination hereof.
16a. The process according to paragraphs 1a-15a, wherein the volatile base adjusts the pH of the protein solution with at least 0.5 pH unit.
17a. The process according to paragraphs 1a-16a, wherein the volatile base adjusts the pH of the protein solution with at least 0.7 pH unit, or at least 0.9 pH unit or at least 1.1 pH unit, or at least 1.3 pH unit or at least 1.5 pH unit.
18a. The process according to paragraphs 1a-17a, wherein the pH of the protein solution is adjusted with a solution comprising sodium hydroxide and ammonium hydroxide.
19a. The process according to paragraphs 1a-18a, wherein the protein solution comprises phenol.
20a. The process according to paragraphs 1a-19a, wherein the protein is selected from the group consisting of insulin, insulin analogues, insulin derivatives, GLP-1, GLP-1 analogues, GLP-1 derivatives, exendin, exendin analogues and derivatives and/or any combination thereof.
21a. The process according to paragraphs 1a-20a, wherein the protein is selected from the group consisting of amylin, amylin analogues, amylin derivatives, α-MSH, α-MSH analogues, α-MSH derivatives and/or any combination thereof.
22a. The process according to paragraphs 1a-20a, wherein the protein solution comprises a protein selected from the group consisting of insulin, insulin analogues, insulin derivatives and the solution further comprises zinc.
23a. The process according to paragraphs 1a-22a, wherein the protein solution comprises a buffer, a detergent, a stabilizer, a protease inhibitor, a flavour, a carrier, an absorption protecting agent, a bulking agent or an agent improving the flowing properties or a penetration enhancer or a combination hereof
24a. The process according to paragraph 23a, wherein the protein solution comprises glycylglycine
25a. The process according to paragraphs 1a-24a, wherein the pH of the protein solution is above the pH of the dried protein.
26a. The process according to paragraph 25a, wherein the pH of the protein solution is at least 0.5 pH units above the pH of the dried protein.
27a. The process according to paragraphs 1a-26a, wherein the pH of the protein solution is at least 0.7, at least 0.9, at least 1.1, at least 1.3 or at least 1.5 pH units above the pH of the of the dried protein.
28a. The process according to paragraphs 1a-27a, wherein the pH of the dried protein is between about 6.0 and about 8.5.
29a. The process according to paragraphs 1a-28a, wherein the pH of the dried protein is between about 6.2 and about 8.4, between about 6.4 and about 8.3, between about 6.6 and about 8.2, between about 6.8 and about 8.1, between about 7.0 and about 8.0, between about 7.2 and about 7.9, between about 7.4 and about 7.8 or between about 7.6 and about 7.7.
30a. The process according to paragraphs 1a-29a, wherein the protein solution is dried to obtain a water content of the spray dried protein below about 10%, below about 6%, below about 4%, below about 2% or below about 1%.
31a. The process according to paragraphs 1a-30a, wherein the protein is an insulin analogue is selected from the group consisting of AspB28 human insulin; LysB28ProB29 human insulin and LysB3GluB29 human insulin.
32a. Dried protein obtainable by the process of paragraphs 1a-31a.
33a. Pharmaceutical composition comprising a therapeutically effective amount of a spray-dried protein according to paragraph 32a.
34a. Pharmaceutical composition according to paragraph 33a wherein the composition is for pulmonary, parenteral, nasal or oral treatment of diabetes or hyperglycaemia.
35a. Pharmaceutical composition for the treatment of diabetes or hyperglycaemia in a patient in need of such treatment, comprising a therapeutically effective amount of a dried protein according to paragraph 32a, wherein the protein is selected from the group consisting of insulin, insulin analogues, insulin derivatives, GLP-1, GLP-1 analogues, GLP-1 derivatives, exendin, exendin analogues and derivatives and/or any combination thereof.
36a. A method of treating diabetes in a patient in need of such a treatment, comprising administering to the patient a therapeutically effective amount of a dried protein according to any of the paragraph 32a or a pharmaceutical composition according to paragraphs 33a-35a.
37a. A method according to paragraph 36a, wherein the protein is selected from the group consisting of insulin, insulin analogues, insulin derivatives, GLP-1, GLP-1 analogues, GLP-1 derivatives, exendin, exendin analogues and derivatives and/or any combination thereof 38a. Dried protein as described in the examples.

Analytical Methods

HMWP content was determined by a isocratic size exclusion chromatography method based on a Ph. Eur method. A Waters Insulin HMWP 7.8×300 mm column was used with a mobile phase consisting of 65% 1.0 mg/ml L-arginine solution, 20% acetonitrile, and 15% glacial acetic acid at a flow of 0.5 ml/min. Injection volumes were 100 µl. The column temperature was ambient. Detection was made by ultraviolet absorbance at 276 nm. Chromatograms were analyzed on a peak area versus total peak area basis.

Purity was determined with a reversed-phase chromatography method utilizing a Waters Sunfire C18, 3.5 µm, 150×4.6 mm i.d. column. The column temperature was 35° C. and the flow rate was 1 ml/min. A gradient system was used with mobile phase A containing 1.4% (w/w) sodium sulfate, 0.2% (w/w) o-phosphoric acid, 7.7% (w/w) acetonitrile, pH 3.6 and mobile phase B containing 42.8% (w/w) acetonitrile in water. The gradient system began isocratically at approximately 42% mobile phase B for 30 min. Mobile phase B was then increase linearly from 42% to 80% over 3 min and remained isocratically for 2 minutes. Initial conditions then returned to 42% mobile phase B over 1 min and was remained for 20 min. Detection was by ultraviolet absorbance at 214 nm. Injection volume was 10 µl. Chromatograms were analysed on a peak area versus total peak area basis. The method detects insulin related impurities including desamido forms of insulin and is reported as insulin related impurities.

The volume particle size distribution of the spray-dried powders was determined using a laser diffraction apparatus, Mastersizer (Malvern Instruments, United Kingdom) operated in wet mode. The apparatus was equipped with a wet dispersion system (Malvern QS Small Volume Sample Dispersion Unit) in which the microparticles was suspended in isopropanol containing approximately 0.05% Tween 80. Then sample is measure and based on the scattering data a particle size distribution is calculated using Malvern software. The volume median diameter D[v,0.5] is the diameter where 50% of the distribution is above and 50% is below.

The aerodynamic particle size distribution of the spray dried powders was determined using a model 3321 Aerodynamic Particle Sizer® (APS) spectrometer (TSI incorporated), which is a laser based particle sizing instrument that measures the aerodynamic diameter of individual particles based on the particles velocities immediately downstream of a flow accelerating nozzle. The powders were aerosolized with a Small Scale powder Disperser model 3433 (TSI incorporated). From these measurements, size distributions are determined in nearly real time. The mass median aerodynamic diameter (MMAD) is the aerodynamic diameter where 50% of the distribution is above and 50% is below.

Residual moisture content of the spray dried powder was determined by loss on drying at 110° C. for minimum 3 hours using a Perkin Elmer Pyris TGA1 thermogravimetric analyzer. The weight change caused by moisture loss was registered and expressed in percent by weight.

EXAMPLES

Example 1

Dissolution of Insulin Human at pH 9.5

10.0 g of insulin human was dispersed in 387.3 g ice cold water. The dispersion was placed on ice bath and the pH was measured to pH 5.03. Ice cold 0.2 N sodium hydroxide was then added step wise until pH 8.99. After 45 minutes pH was decreased to 8.77 and over the next 4 hours ice cold 0.2 N sodium hydroxide was added until pH 8.75. The solution was still not clear and it was placed in a refrigerator over night.

The next day pH was measured to 8.75 and the solution was still not clear. pH was adjusted to 9.48 witch ice cold 0.2 N sodium hydroxide and the unclear solution was then placed in the refrigerator for the next 5 days.

After 5 days the solution was clear and pH was adjusted from 9.37 until 7.59 with 0.2 N hydrogen chloride.

Example 2

A) Spray drying of protein solution with volatile base and
B) Measurement of pH of spray dried protein 9.5 g of insulin human was dispersed in 200 g ice cold water. The suspension was placed on ice bath and the initial pH was measured to pH 5.12. The pH was adjusted to 7.04 with 5.8 g of ice cold 0.2 N sodium hydroxide. The solution remained on ice bath for another 2 hour and then demineralised water was added to a total weight of 240 g.

50 g of the pH 7.04 solution was further processed. The pH was adjusted from 7.04 to 7.50 witch ice cold 1 N NH$_4$OH and was then placed in a refrigerator overnight. The next day pH was measured to 7.32 and pH was adjusted with ice cold 1 N NH$_4$OH to pH 8.06. Then water was added up to 60.0 g. The final concentration of insulin human was approximately 30 mg/ml.

Dry, solid microparticles were prepared on a Büchi B-290 mini spray dryer (Büchi, Labortechnik AG Flawil, Switzerland) equipped with a 0.7 mm co-current two-fluid nozzle. The insulin human solution was atomised into hot air stream in a drying chamber at a liquid feed rate of 2 ml/min and atomising air flow of 600-800 liter/hour.

The drying air had an inlet temperature of 150° C. and a drying air flow rate of 35 m$^3$/hour. The outlet temperature was approximately 70° C.

Solid microparticles were captured by a cyclone connected to the drying chamber and then gathered and stored at dry conditions.

Spray dried insulin human (protein solution pH was 8.06 before spray drying) were re-dissolved in demineralised water at concentrations at 40 mg/mL, 80 mg/mL and 160 mg/mL to investigate if the different concentrations have influence of the measured pH value:

25.3 mg was added 633 µL water: pH was measured to 6.95
43.5 mg was added 545 µL water: pH was measured to 6.95
81.7 mg was added 510 µL water: pH was measured to 7.01

Example 3

Spray drying of insulin aspart (B28$^{Asp}$ human insulin) dissolved by various ratio of volatile and non-volatile base.

Various insulin aspart solutions with and without stabilising excipients were prepared prior to spray drying:

Preparation A

Solution A1: 16 g insulin aspart was suspended in 150 ml water on an ice bath. Next, 2.6 ml of ice cold concentrated aqueous ammonia (25% w/w) was added stepwise until pH was 7.53 and a clear solution was optained. Finally, water was added to a total volume of 200 ml. The concentration of insulin aspart was 80 mg/ml.

Solution A2: 65 ml of solution A1 was diluted further to 130 ml. The concentration of insulin aspart was 40 mg/ml.

Preparation B

Solution B1: 16 g insulin aspart was suspended in 150 ml water on an ice bath. Initially, 2.2 ml of ice cold 1 N NaOH and then 750 µl ice cold concentrated aqueous ammonia (25% w/w) was added stepwise until pH was 7.52 and a clear solution was optained. Finally, water was added to a total volume of 200 ml. The concentration of insulin aspart was 80 mg/ml.

Solution B2: 65 ml of solution B1 was diluted further to 130 ml. The concentration of insulin aspart was 40 mg/ml.

Preparation C

Solution C1: 16 g insulin aspart was suspended in 150 ml water on an ice bath. Initially, 4.4 ml of ice cold 1 N NaOH and then 750 µl ice cold concentrated aqueous ammonia (25% w/w) was added stepwise until pH was 7.48 and a clear solution was optained. Finally, water was added to a total volume of 200 ml. The concentration of insulin aspart was 80 mg/ml.

Solution C2: 65 ml of solution C1 was diluted further to 130 ml. The concentration of insulin aspart was 40 mg/ml.

Preparation D

Solution D1: 16 g insulin aspart was suspended in 150 ml water on an ice bath. Initially, 6.6 ml of ice cold 1 N NaOH and then 370 µl ice cold concentrated aqueous ammonia (25% w/w) was added stepwise until pH was 7.47 and a clear solution was optained. Finally, water was added to a total volume of 200 ml. The concentration of insulin aspart was 80 mg/ml.

Solution D2: 65 ml of solution D1 was diluted further to 130 ml. The concentration of insulin aspart was 40 mg/ml.

Preparation E

Solution E1: 16 g insulin aspart was suspended in 150 ml water on an ice bath. Initially, 6.6 ml of ice cold 1 N NaOH and then 370 µl ice cold concentrated aqueous ammonia (25% w/w) was added stepwise until pH was 7.47 and a clear solution was optained. Finally, water was added to a total volume of 200 ml. The concentration of insulin aspart was 80 mg/ml.

Solution E2: 65 ml of solution E1 was diluted further to 130 ml. The concentration of insulin aspart was 40 mg/ml.

Preparation F 1.8 g insulin aspart was suspended in 40 ml water on an ice bath. Initially, 175 µl ice cold concentrated aqueous ammonia (25% w/w) was added stepwise until pH was 7.83.

1.1 ml of a 0.1 M ZnCl$_2$ solution and 3.6 ml of a 0.32 M phenol solution was further added to the solution.

Finally, pH was adjusted to 7.99 with 85 μl of diluted aqueous ammonia (8% w/w) and water was added to a total volume of 60 ml. The solution was clear and the concentration of insulin aspart was 30 mg/ml.

Preparation G 1.8 g insulin aspart was suspended in 40 ml water on an ice bath. Initially, 288 μl of ice cold 1 N NaOH and then 120 μl ice cold concentrated aqueous ammonia (25% w/w) was added stepwise until pH was 7.86.

1.1 ml of a 0.1 M $ZnCl_2$ solution and 3.6 ml of a 0.32 M phenol solution was further added to the solution.

Finally, pH was adjusted to 8.03 with 80 μl of diluted aqueous ammonia (8% w/w) and water was added to a total volume of 60 ml. The solution was clear and the concentration of insulin aspart was 30 mg/ml.

Preparation H 1.8 g insulin aspart was suspended in 40 ml water on an ice bath. Initially, 864 μl of ice cold 1 N NaOH and then 50 μl ice cold concentrated aqueous ammonia (25% w/w) was added stepwise until pH was 7.85.

1.1 ml of a 0.1 M $ZnCl_2$ solution and 3.6 ml of a 0.32 M phenol solution was further added to the solution.

Finally, pH was adjusted to 7.98 with 60 μl of diluted aqueous ammonia (8% w/w) and water was added to a total volume of 60 ml. The solution was clear and the concentration of insulin aspart was 30 mg/ml.

Preparation I 1.8 g insulin aspart was suspended in 40 ml water on an ice bath. Initially, 150 μl ice cold concentrated aqueous ammonia (25% w/w) was added stepwise until pH was 7.99.

4.6 ml of a 0.25 M glycylglycine solution, 1.1 ml of a 0.1 M $ZnCl_2$ solution and 3.6 ml of a 0.32 M phenol solution was further added to the solution.

Finally, pH was adjusted to 7.98 with 245 μl of diluted aqueous ammonia (8% w/w) and water was added to a total volume of 60 ml. The solution was clear and the concentration of insulin aspart was 30 mg/ml.

Preparation J 1.8 g insulin aspart was suspended in 40 ml water on an ice bath. Initially, 288 μl of ice cold 1 N NaOH and then 125 μl ice cold concentrated aqueous ammonia (25% w/w) was added stepwise until pH was 8.18.

4.6 ml of a 0.25 M glycylglycine solution, 1.1 ml of a 0.1 M $ZnCl_2$ solution and 3.6 ml of a 0.32 M phenol solution was further added to the solution.

Finally, pH was adjusted to 7.98 with 125 μl of diluted aqueous ammonia (8% w/w) and water was added to a total volume of 60 ml. The solution was clear and the concentration of insulin aspart was 30 mg/ml.

Preparation K 1.8 g insulin aspart was suspended in 40 ml water on an ice bath. Initially, 288 μl of ice cold 1 N NaOH and then 125 μl ice cold concentrated aqueous ammonia (25% w/w) was added stepwise until pH was 7.93.

1.1 ml of a 0.1 M $ZnCl_2$ solution and 1.9 ml of a 0.32 M phenol solution was further added to the solution.

Finally, pH was adjusted to 7.98 with 40 μl of diluted aqueous ammonia (8% w/w) and water was added to a total volume of 60 ml. The solution was clear and the concentration of insulin aspart was 30 mg/ml.

Dry, solid microparticles were prepared on a Büchi B-290 mini spray dryer (Büchi, Labortechnik AG Flawil, Switzerland) equipped with a 0.7 mm co-current two-fluid nozzle. The liquid feed (preparation A1, A2, B1, B2, C1, C2, D1, D2, E1, E2, F, G, H, I, J, and K) was atomised into hot air stream in a drying chamber at a liquid feed rate of 2 ml/min and at an atomising air flow of 600-800 liter/hour.

The drying air had an inlet temperature of 150° C. and a drying air flow rate of 35 $m^3$/hour. The outlet temperature varied between 41 and 61° C.

Solid microparticles were captured by a cyclone connected to the drying chamber and then gathered and stored at dry conditions.

Insulin chemical instability was studied by HPLC analysis as described in Hvass, 2003, (A. Hvass, M. Hach, and M. U. Jars. Complementary analytical HPLC methods for insulin-related degradation products. American Biotechnology Laboratory 21 (2): 8-12, 2003) following storage for 1 month at 40° C. Covalent-bound dimer and high molecular weight polymers (HMWP) were analysed size exclusion (SE) chromatography. Reverse-phase (RP) chromatography (pH 3.6) with gradient elution was used in the separation of degradation products (desamido forms of insulin and other insulin related impurities).

Moisture content of the dry microparticles was determined by loss on drying at 110° C. for minimum 3 hours using a Perkin Elmer Pyris TGA1 thermogravimetric analyzer. The weight change caused by moisture loss was registered and expressed in percent by weight.

An Aerodynamic Particle Sizer® spectrometer (APS) was used to determine particle size distribution (mass median aerodynamic diameter).

pH of the spray dried insulin was measured by dissolving the spray dried powders in demineralised water to a concentration of approximately 40 mg/ml and measuring pH by a potentiometer (Radiometer, Denmark).

The results from characterisation of the spray dried preparations A-K is listed in Table 1.

TABLE 1

Spray dried insulin aspart powders

| Preparation ID | Moisture (%) | Solution pH | pH of the spray dried insulin | $MMAD^{4)}$ (μm) | Insulin aspart related impurities[B] (%) | $HMWP^{C)}$ (%) |
|---|---|---|---|---|---|---|
| A1 | 5.6 | 7.5 | 5.35 | 2.7 | 1.1 | 0.43 |
| A2 | 6.6 | 7.5 | 6.03 | 3.3 | 1.4 | 0.45 |
| B1 | 6.3 | 7.5 | 6.04 | 3.0 | 1.1 | 2.17 |
| B2 | 7.0 | 7.5 | 6.17 | 4.8 | 1.3 | 0.75 |
| C1 | 6.7 | 7.5 | 6.27 | 3.3 | 0.8 | 0.63 |
| C2 | 7.1 | 7.5 | 6.44 | 4.0 | 1.4 | 0.67 |
| D1 | 5.9 | 7.5 | 6.66 | 3.3 | 0.3 | 0.26 |
| D2 | 5.8 | 7.5 | 6.89 | 3.9 | 1.0 | 2.87 |
| E1 | 6.6 | 7.5 | 7.43 | 3.2 | 0.4 | 0.22 |
| E2 | 5.2 | 7.5 | 7.43 | 3.9 | 0.7 | 0.31 |

TABLE 1-continued

Spray dried insulin aspart powders

| Preparation ID | Moisture (%) | Solution pH | pH of the spray dried insulin | MMAD[A] (μm) | Insulin aspart related impurities[B] (%) | HMWP[C] (%) |
|---|---|---|---|---|---|---|
| F | 6.9 | 8.0 | 4.91 | 2.6 | 2.0 | 0.35 |
| G | 9.3 | 8.0 | 5.16 | 2.6 | 1.9 | 0.51 |
| H | 9.6 | 8.0 | 6.33 | 2.8 | 1.4 | 0.35 |
| I | 7.2 | 8.0 | 5.04 | 2.7 | 2.3 | 0.30 |
| J | 8.2 | 8.0 | 5.79 | 2.8 | 1.9 | 0.24 |
| K | 8.9 | 8.0 | 5.37 | 2.7 | 1.8 | 0.47 |

[A]MMAD is the mass median aerodynamic diameter determined by APS
[B]Insulin aspart related impurities formed following storage for 1 month at 40° C., measured by RP-HPLC (including desamido and other degradation forms of insulin aspart)
[C]High molecular weight polymers formed following storage for 1 month at 40° C., measured by SE-HPLC Example 4

Spray Drying of Insulin Aspart 361.8 g insulin aspart was dispersed in 4.5 liter ice cold demineralised water. The pH was adjusted to 7.68 with ice cold 0.2 NaOH. Water was added up to 9 liter. The final concentration of insulin aspart was 37 g/l. The solution was filtered through a sterile filter (0.2 μm) before spray drying.

Spray drying of the insulin aspart solution was performed on pilot scale spray dryer (model Mobile Minor, Niro, Denmark) with a two-fluid nozzle with a 1.0 mm orifice diameter. Nitrogen was used both as drying gas and as atomisation gas.

The inlet and outlet temperatures were 110 and 62° C., respectively. The feed flow was approximately 1 kg/h and the gas/feed ratio was approximately 11.

The spray dryer was equipped with both a cyclone and bag filters. The powder was collected simultaneously from both the cyclone and the bag filters during spray drying.

Particle size distribution was analysed by both laser diffraction (Mastersizer, Malvern) and aerodynamic particles sizing spectroscopy (APS). The chemical integrity of spray dried insulin aspart following storage at 1 month at 40° C. was studied by SE og RP-HPLC as described in example 2.

| | Cyclone fraction | Bag filter fraction |
|---|---|---|
| D50[A] (μm) | 4.2 | 2.5 |
| MMAD[B] (μm) | 3.5 | 2.1 |
| Yield (%) | 78 | 23 |
| HMWP formed per month at 40° C. (%) | 0.2 | 0.4 |
| Insulin related impurities formed per month at 40° C. (%) | 0.8 | 1.3 |

[A]D50 is the volume median diameter determined by laser diffraction
[B]MMAD is the mass median aerodynamic diameter determined by APS Example 5

Storage Stability of Freeze Dried Insulin Aspart Dry Powders with Various pH Values 0.806 g of insulin aspart was dispersed in 10 ml ice cold water. The suspension was placed on ice bath and the initial pH was measured to pH 4.58. The pH was adjusted to 7.39 with ice cold 0.2 N sodium hydroxide, hereby solubilising the insulin aspart. Demineralised water was added to a total weight of 20.4 g.

The solubilised insulin aspart was divided into 6 aliquots of 2.5 ml, which were adjusted to pH 7.0, 7.7, 8.0, 8.5, 9.0 and 9.5 respectively. Demineralised water was added to a total weight of 3.06 g.

The insulin aspart solutions were freeze-dried in a Christ Alpha 2-4 LSC (Christ Alpha, Germany) apparatus in aliquots of 0.9 ml in glass vials using a standard freeze drying program.

pH of the freeze dried insulin aspart powders were measured by adding 0.5 ml of demineralised water to approximately 33 mg of insulin aspart powder and then measuring pH with a potentiometer equipped with a pH electrode after 15 minutes.

The chemical integrity of spray dried insulin aspart following dry (above silica gel) storage for 2 weeks at 40° C. relative to controls at −18° C. was studied by SE-HPLC as described in example 2.

TABLE 3

Freeze dried insulin aspart powders

| Solution pH | pH of the freeze dried insulin | HMWP[A] (%) |
|---|---|---|
| 7.0 | 6.69 | 0.20 |
| 7.7 | 7.58 | 0.17 |
| 8.0 | 7.83 | 0.11 |
| 8.5 | 8.42 | 0.07 |
| 9.0 | 8.81 | 0.10 |
| 9.5 | 9.27 | 0.10 |

[A]High molecular weight dimers and polymers formed following storage for 2 weeks at 40° C., measured by SE-HPLC Example 6

Storage Stability of Spray Dried Insulin Aspart Dry Powders with Various pH Values 20.6 g of insulin aspart was dispersed in 300 ml ice cold water. The suspension was placed on ice bath and the initial pH was measured to pH 4.63. The pH was adjusted to 7.50 with 100 ml of ice cold 0.1 N sodium hydroxide, hereby solubilising the insulin aspart.

The solubilised insulin aspart was divided into 6 aliquots 65 g, which were adjusted to pH 7.0, 7.7, 8.0, 8.5, 9.0 and 9.5 respectively with ice cold 0.1 N NaOH. Demineralised water was added to each aliquot to a total weight of 80.0 g. The concentration of insulin aspart was approximately 38 mg/ml.

Dry, solid microparticles were prepared on a Büchi B-290 mini spray dryer (Büchi, Labortechnik AG Flawil, Switzerland) equipped with a 0.7 mm co-current two-fluid nozzle. The liquid feed (80 ml) was atomised into hot air stream in a drying chamber at a liquid feed rate of 2 ml/min and at an atomising air flow of 600-800 liter/hour.

The drying air had an inlet temperature of 150° C. and a drying air flow rate of 35 m³/hour. The outlet temperature varied between 49 and 61° C. Solid microparticles were captured by a cyclone connected to the drying chamber and then gathered and stored at dry conditions.

pH of the spray dried insulin aspart was measured by dissolving the spray dried powders in demineralised water to a concentration of 70-80 mg/ml and measuring pH by a potentiometer (Radiometer, Denmark).

The chemical integrity of spray dried insulin aspart following dry (above silica gel) storage for 4 weeks at 40° C. relative to controls at −18° C. was studied by SE-HPLC and RP-HPLC as described in example 2.

TABLE 3

Stability of spray dried insulin aspart powders

| Solution pH | pH of the spray dried insulin aspart | HMWP[A] (%) | Purity[B] (%) |
|---|---|---|---|
| 7.5 | 7.28 | 0.28 | 98.2 |
| 7.7 | 7.54 | 0.26 | 98.3 |
| 8.0 | 7.82 | 0.22 | 98.3 |
| 8.5 | 8.26 | 0.19 | 98.4 |
| 9.0 | 8.58 | 0.23 | 98.2 |
| 9.5 | 9.00 | 1.34 | 95.0 |

[A]High molecular weight dimers and polymers formed following storage for 4 weeks at 40° C., measured by SE-HPLC
[B]Purity of spray dried insulin aspart following storage for 4 weeks at 40° C., measured by RP-HPLC Example 7

20000 nmol of a lysine-acylated GLP1 analogue N-epsilon26-[2-(2-{2-[2-(2-{2-[(S)-4Carboxy-4-(17carboxyheptadecanoylamino)butyrylamino]ethoxy}ethoxy)acetylamino]-ethoxy}ethoxy)acetyl][Aib8,Arg34]GLP-1-(7-37) was dissolved in water to 4000 nmol/mL (molecular weight 4113 g/mol). 2 mL of the solution was adjusted to pH 7.6 by sodium hydroxide and further divided in 2 parts of which one was added ammonia (25% in water) to pH 9.6. Similarly 2 mL solution was added sodium hydroxide to pH 8.7, divided in 2 parts and one added ammonia (25% in water) to pH 10.3. Finally 1 mL GLP1 analogues solution was added sodium hydroxide to pH 10.3. The 5 samples were all freeze dried and redissolved to 40 mg/mL. pH values were measured in the samples to respectively 7.5, 7.5, 8.6, 8.6 and 9.7.

Example 8

Spray Drying of a GLP-1 Analogue with Volatile Base 180 mg (43800 nmol) of a lysine-acylated GLP1 analogue N-epsilon26-[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetyl][Aib8,Arg34]GLP-1-(7-37) was dissolved in 7 ml of demineralised water and pH was adjusted from pH 7.53 to pH 7.03 with 0.2 N hydrochloric acid. Then the solution was adjusted to pH 9.96 with 0.25% w/w aqueous ammonia and demineralised water was added to give a final concentration of GLP-1 analogue of 20 mg/ml.

The solution was atomised into hot air stream in a drying chamber of a Büchi B-290 mini spray dryer (Büchi, Labortechnik AG Flawil, Switzerland) equipped with a 0.7 mm co-current two-fluid nozzle at a liquid feed rate of 2 ml/min and at an atomising air flow of 600-800 liter/hour. The drying air had an inlet temperature of 150° C. and a drying air flow rate of 35 m3/hour. The outlet temperature was approximately 63° C. Solid microparticles were captured by a cyclone connected to the drying chamber.

The powder was redissolved in demineralised water to 120 mg/ml and pH was measured to pH 6.9.

Example 9

Chemical Instability of Insulin Aspart at Strongly Alkaline pH Values 720 mg of insulin aspart was solubilized in 9 ml of demineralised water. 2.25 ml of the solution was adjusted from pH 7.6 to pH 10.0 with a 2 N ammonium hydroxide solution. Another 2.25 ml of the solution is adjusted to pH 11.0 with a 2 N ammonium hydroxide solution. Yet another 2.25 ml of the solution was adjusted to pH 12.0 with a 2 N ammonium hydroxide solution and a 1 N sodium hydroxide solution. And finally 2.25 ml of the solution was adjusted to pH 12.6 with a 2 N ammonium hydroxide solution and a 1 N sodium hydroxide solution.

The four pH adjusted solutions were kept in the refrigerator at 3-8° C. for 24 hours ater which the four solutions were adjusted to neutral pH with 1 N hydrochloric acid in order to quench the chemical degradation.

Insulin chemical instability in the neutralised solutions was studied by size exclusion and reverse phase HPLC analysis as described in example 2.

TABLE 4

Chemical stability of insulin aspart solutions at various pH values

| Solution pH | HMWP[A] (%) | Purity[B] (%) |
|---|---|---|
| 7.6 | 0.0 | 97.2 |
| 10.0 | 0.5 | 97.8 |
| 11.0 | 1.8 | 92.2 |
| 12.0 | 49.8 | 7.8 |
| 12.6 | 39.5 | 2.3 |

[A]High molecular weight dimers and polymers formed following storage for 24 hours at 3-8° C., measured by SE-HPLC
[B]Purity of insulin aspart following storage for 24 hours at 3-8° C., measured by RP-HPLC

The invention claimed is:

1. A process for drying a protein solution to obtain a dried protein with a specified pH, the process comprising:
   a) selecting a target pH for the dried protein, wherein the target pH for the dried protein is between 6.0 and 8.5,
   b) selecting a target pH for the protein solution wherein the target pH for the protein solution is at least about 0.5 pH units above the target pH for the dried protein selected in step (a), and wherein the target pH for the protein solution is between 7.4 and 11.0,
   c) obtaining the protein solution at a temperature below 8° C. by steps (i)-(v), wherein the steps (ii)-(v) can be carried out in any order while stirring continuously,
      i. providing an aqueous phase,
      ii. adding a protein,
      iii. optionally adding excipients,
      iv. adjusting the pH with a non-volatile base and optionally a non-volatile acid to the target pH for the dried protein selected in step (a),
      v. adjusting the pH with a volatile base to the target pH for the protein solution selected in step (b), and
   d) drying the protein solution resulting from step (c) to obtain a dried protein with a pH selected in step (a),
   and wherein the protein is selected from the group consisting of insulin, insulin analogues, insulin derivatives, GLP-1, GLP-1 analogues, GLP-1 derivatives, glucagon and/or any combination thereof.

2. The process according to claim 1, wherein step (v) comprises adjusting the pH of the protein solution by at least 0.5 pH unit with the volatile base.

3. The process according to claim 1, comprising in step (iii) adding an excipient selected from a buffer, a detergent, a stabilizer, a protease inhibitor, a flavour, a carrier, an absorption protracting agent, a bulking agent, an agent improving the flowing properties, a penetration enhancer, or a combination hereof.

4. The process according to claim 1, comprising in step (iii) adding glycylglycine and/or phenol.

5. The process according to claim 4, comprising in step (iii) adding about 4 moles of phenol per mole of protein.

6. The process according to claim 1, wherein the drying method is selected from the group consisting of spray drying, spray freeze drying, fluid bed drying, freeze drying and vacuum drying.

7. The process according to claim 1, wherein the target pH of the protein solution in step (b) is at least about 0.7 pH units above the target pH of the dried protein.

8. The process according to claim 7, wherein the target pH of the protein solution in step (b) is at least about 0.9 pH units above the target pH of the dried protein.

* * * * *